United States Patent [19]

Yamamoto et al.

[11] Patent Number: 5,725,864
[45] Date of Patent: Mar. 10, 1998

[54] COMPOSITION FOR SUPPRESSING INFECTION AND GROWTH OF HUMAN IMMUNODEFICIENCY VIRUS

[75] Inventors: Naoki Yamamoto; Hideki Nakashima, both of Tokyo; Wataru Motsuchi, Sagamihara; Shigeaki Tanaka, Ayase; Shunichi Dosako, Urawa; Hiroshi Shinmoto, Kawagoe, all of Japan

[73] Assignee: Snow Brand Milk Products Co., Ltd., Hokkaido, Japan

[21] Appl. No.: 361,862

[22] Filed: Dec. 22, 1994

Related U.S. Application Data

[63] Continuation of Ser. No. 97,848, Jul. 27, 1993, abandoned.

[30] Foreign Application Priority Data

Jul. 28, 1992 [JP] Japan .................................. 4-220635

[51] Int. Cl.$^6$ ...................... A01N 37/18; A61K 38/16; A61K 38/00; C07K 2/00
[52] U.S. Cl. .................... 424/278.1; 514/6; 514/8; 514/12; 514/21; 530/300; 530/350
[58] Field of Search ................ 424/278.1; 514/21, 514/8, 6; 500/300, 350

[56] References Cited

U.S. PATENT DOCUMENTS

| | | | |
|---|---|---|---|
| 4,448,762 | 5/1984 | Richards et al. | 424/1.1 |
| 4,918,008 | 4/1990 | Gauri | 435/68.1 |
| 4,977,137 | 12/1990 | Nichols et al. | 514/6 |
| 5,164,486 | 11/1992 | Tsunoo et al. | 424/85.8 |
| 5,198,419 | 3/1993 | Ando et al. | 514/8 |
| 5,214,028 | 5/1993 | Tomita et al. | 514/6 |

FOREIGN PATENT DOCUMENTS

| | | |
|---|---|---|
| 0406416A1 | 1/1991 | European Pat. Off. . |
| 0559425A1 | 9/1993 | European Pat. Off. . |
| 0584558 | 3/1994 | European Pat. Off. ....... A61K 37/02 |
| WO92/21752 | 12/1992 | WIPO . |

OTHER PUBLICATIONS

Legrand D. et al., "Characterization and Localization of an Iron–Binding 18–kDa Glycopeptide isolated From the N–Terminal Half of Human Lactoferrin", Biochimica et Biophysica Acta, 787, 90–96 (1984).
Tani F. et al., "Isolation and Characterization of Opioid Antagonist Peptides Derived From Human Lactoferrin", Agric. Biol. Chem. 54, 1803–1810 (1990).
Saito H. et al., "Potent Bactericidal Activity of Bovine Lactoferrin Hydrolysate Produced by Heat Treatment at Acidic pH", J. Dairy Science, 74, 3724–3730 (1991).
Richie et al, J. Reproductive Immunology. 12(2):137–148, 1987.
Brock. Archives of Disease in Childhood, 55:417–421, 1980.
Esaguy et al. 1993. Scand. J. Immunol. 38:147–152.
Haynes. 1993. Science. 260:1279–1286.
Niu et al. 1993. J. Infect. Dis. 168:1490–501.
Fox. 1994. Bio/Technology 12:128.
Brock 1980. Archives of Diseases in Childhood 55:417–421.
Sandstrom et al. 1987. Drugs 34:372–390.
Koff et al 1988. Development and Testing of AIDS Vaccines. Science 241:426–432.
Schild et al. 1990. Modern Vaccines. Lancet vol. 335:1081–84.
Letvin. 1993. Vaccines Against Human Immuno–Deficiency Virus . . . New England J. Medicine 329(19):1400–1405.
Fuchs et al., "Association Between Immune Activation, Changes of Iron Metabolism and Anaemia in Patients With HIV Infection," Eur J Haematol, 50:90–94 (1993).
Kotler et al., "Enteral Alimentation and Repletion of Body Cell Mass in Malnourished Patients With Acquired Immunodeficiency Syndrome," Am J. Clin Nutr., 53:149–54 (1991).
Letendre, "The Importance of Iron in the Pathogenesis of Infection and Neoplasia," TIBS, 166–168 (Apr., 1985).
Miles et al., "Recombinant Human Granulocyte Colony–Stimulating Factor Increases Circulating Burst Forming Unit–Erythron and Red Blood Cell Production in Patients With Severe Human Immuno–deficiency Virus Infection".: Blood, 75:2137–2142 (1990).
Blumberg et al., "Iron and Iron Binding Proteins in Persistent Generalised Lymphadenopathy and Aids," The Lancet, p. 347 (Feb., 1984).

Primary Examiner—Nita Minnifield
Attorney, Agent, or Firm—Testa, Hurwitz & Thibeault, LLP

[57] ABSTRACT

The invention relates to compositions and methods for inhibiting infection or suppressing growth of human immunodeficiency virus. The composition comprises, as an effective component, an iron-binding protein (e.g., lactoferrin, transferrin, ovotransferrin), a chemically modified compound of the iron-binding protein, or a hydrolyzed compound of the iron-binding protein. The effective components are safe and can be easily prepared from inexpensive raw materials. The composition can be orally administered, injected or applied to the skin, eye, ear, nose or used as a preparation for vagina affusion, mouth washing or suppositories, and can effectively inhibit infection or suppress growth of human immunodeficiency virus.

13 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly  Arg  Arg  Gly
    1

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:2:

Gly Arg Arg Arg Arg Gly
1               5

( 2 ) INFORMATION FOR SEQ ID NO:3:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:3:

Gly Arg Lys Gly
1

( 2 ) INFORMATION FOR SEQ ID NO:4:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Gly Lys Lys Gly
1

COMPOSITION FOR SUPPRESSING INFECTION AND GROWTH OF HUMAN IMMUNODEFICIENCY VIRUS

This is a continuation of application Ser. No. 08/097,848 filed on Jul. 27, 1993 now abandoned.

BACKGROUND OF THE INVENTION

1. Field of the Invention

The present invention relates to a composition for inhibiting infection or suppressing growth of human immunodeficiency virus, comprising an iron-binding protein, a chemically modified compound of the iron-binding protein, or hydrolysate of an iron-binding protein, as an effective component.

2. Description of the Background Art

Acquired Immune Deficiency Syndrome (AIDS) is a serious immune deficiency disease caused by infection of human immunodeficiency virus (HIV). As of July 1993, the number of AIDS patients reported to WHO is 370,000 and the actual number of HIV infected patients are supposed to be well over that number. At first, HIV infection was considered to be a characteristic infection disease for homosexuals, drug-abusers, and the like. Nowadays, a heterosexual intercourse is proven to be the most significant infection route.

Methods to cure AIDS which are currently being developed include a reverse transcriptase inhibitor, a virus adsorption inhibitor, a protease inhibitor, a sugar chain synthesis inhibitor, a neutralizing antibody, a passive immunization, vaccine, an antisense agent, an immunomodulator, a gene therapy, and the like. Among them, the method using an adsorption inhibitor is very important, because it can act at the earliest stage of the infection and prevent HIV from entering bodies or infecting other cells in vivo.

Many of the methods developed using adsorption inhibitors are related to CD4 of leucocyte differentiation antigen which is a receptor of HIV. They aim to inhibit HIV infection using CD4 itself or CD4 molecule modified with toxin or antibody (Japanese Patent Laid-open (kokai) Nos. 53894/1991, 35781/1991, 311493/1990, Nikkei Bio-technology annual report, 1991/92, 251-260). Beside these research and development activities, a method of administering an inhibitor, which competes with the virus for receptors, using a peptide called peptide T, a method administering T-22 which is a derivative from Polyphemusin or Tachyplesin (a biophylactic peptide originated from a horse foot) (Nakajima, Yamamoto, *Igakukai Newspaper*, No. 1991, Apr. 20, 1992), and the like are being developed.

These adsorption inhibitors are manufactured by recombinant DNA technique or chemical synthesis. Their safety when they are dosed into bodies is unknown. In addition, their production cost is comparatively high. Development of a safe and inexpensive HIV adsorption inhibiting method is therefore strongly desired for the world-wide prevention of AIDS.

On the other hand, according to a patent application related to an anti-virus agent using milk protein (Japanese Patent Laid-open (kokai) No. 233226/1989), lactoferrin is effective for envelop viruses and no-envelop viruses. HIV is also one of envelop viruses. Viruses illustrated in Japanese Patent Laid-open (kokai) No. 233226/1989, however, are herpes simplex virus Type 1, herpes simplex virus Type 2, cytomegalovirus, vesicular stomatitis virus, and rhabdovirus group. Nothing is disclosed concerning HIV or their actions on HIV. HIV is much different from these viruses biologically. Even though there is a report suggesting a relationship between HIV infection and lactoferrin because of a low concentration of lactoferrin in a saliva from HIV patient (Muler et al., Journal of Acquired Immunedeficiency Syndromes 5, 46–51, (1992)). However, no suggestion is given about the action of lactoferrin on inhibiting HIV infection and suppressing growth of HIV.

The present inventors previously found that lactoferrin possesses an effect of inhibiting infection of influenza virus or cytomegalovirus, and filed an application for patent based on this finding (Japanese Patent Laid-open (kokai) No. 233619/1989). In the course of a further study on the anti-virus activity of lactoferrin, the present inventors have found that iron-binding proteins such as lactoferrin also exhibit a strong effect of preventing infection of HIV.

The present inventors have conducted screening of various naturally occurring compounds using a system for detecting HIV-virus infection having excellent reproducibility, and as a result found that iron-binding proteins, chemically modified compounds thereof, or hydrolysate thereof possess an activity of inhibiting infection and suppressing growth of HIV. This finding has led to the completion of the present invention.

HIV is considered to enter into cells via CD4 molecules expressed on the surface of lymphocytes as a receptor. Many of the cells expressing CD4 are T-cells responsible for immune system. HIV has been elucidated to infect other cells which develop CD4. HIV virus particles have a glycoprotein called gp120 on their surface. The binding of the gp120 to CD4 on the target cell triggers the infection. Once the cell is infected, the virus expresses gp120 on the host cell surface. Cells infected with HIV expresses gp120 on their surface when they produce virus. The HIV infection inhibitive effect and the HIV growth suppressing effect, therefore, can be judged by the presence of gp120 on the cell surface.

The present invention has been accomplished in order to solve the aforementioned problems involved in the known therapeutic method comprising inhibiting the HIV adsorption and to effectively inhibit the infection and suppress growth of HIV. Accordingly, the present invention has as its object the provision of a method of preventing or curing AIDS by the use of a component which can be obtained from comparatively inexpensive materials and effective for inhibiting the infection and suppressing the growth of HIV.

SUMMARY OF THE INVENTION

An object of the present invention is to provide a composition for inhibiting infection or suppressing the growth of human immunodeficiency virus comprising, as an effective component, an iron-binding protein, a chemically modified compound thereof, or hydrolysate thereof.

In a preferred embodiment of the present invention said iron-binding protein is lactoferrin, transferrin, or ovotransferrin, and said hydrolysate of the iron-binding protein is an enzymatically or chemically hydrolyzed compound of said iron-binding protein.

In another preferred embodiment of the present invention said iron-binding protein is a chemically modified compound of lactoferrin, in which a peptide containing basic amino acid or a polyamine is bonded.

Other and further objects, features and advantages of the present invention will appear more fully from the following description.

DETAILED DESCRIPTION OF THE INVENTION AND PREFERRED EMBODIMENTS

In the present invention, an iron-binding protein such as lactoferrin, transferrin, ovotransferrin, or the like is used as the effective component. Lactoferrin can be prepared from milk or fluids secreted by mammals; transferrin from blood or tissues of animals; and ovotransferrin from eggs or the like of birds. All of them can be prepared by known methods. For example, lactoferrin is an iron-binding protein separated from milk of mammals and any types of milks from any mammal can be used for the purpose of the present invention. It can be produced by the recombinant DNA technique, if necessary. Lactoferrin currently most inexpensive and easily available is isolated from cow milk. For the isolation of lactoferrin from cow milks an anti-lactoferrin antibody disclosed by Japanese Patent Laid-open (kokai) No. 145200/1986 can be used.

Ovotransferrin is a glycoprotein having a molecular weight of 77,000 to 87,000 which is contained in egg white of chicken. It is an iron-binding protein similar to lactoferrin. Ovotransferrin can be separated and purified by a known chromatographic method or the like, for example, a method using carboxymethyl cellulose (Journal of Food Science, 45, 460 (1980)), a method of using a metal-fixed affinity chromatography (Agricultural Biological Chemistry, 51, 2881–2887 (1987)), and the like. Transferrin can be collected from materials such as blood and the like, and purified also by such means as chromatography or the like.

The hydrolysis treatment of these proteins can be carried out using a protease, such as trypsin, pepsin, papain, thermolysin, subtilisin, or the like, or by a chemical compound, such as hydrochloric acid, sulfuric acid, sodium hydroxide, or the like.

For example, lactoferrin can be limitedly hydrolyzed by an enzyme. For instance, lactoferrin is dissolved into a 0.1M Tris-HCl buffer solution (pH 8.2) containing 0.025M calcium chloride to prepare a concentration of 1%, and then trypsin is added to the lactoferrin solution at a ratio of 1:50, followed by incubation at 37° C. for 4 hours. Fragments with molecular weights of 30,000 and 50,000 can be obtained by the gel filtration of the product in 10% acetic acid solution (Biochem. Biophys. Acta., 787, 90–96 (1984)). In another example, a pepsin hydrolyzed product of lactoferrin can be prepared by dissolving 80 mg of lactoferrin in 8 ml of water, adjusting pH to 1.4 with concentrated hydrochloric acid, incubating in the presence of 1.6 mg of pepsin at 37° C. for 6 hours, and inactivating the enzyme under boiling, followed by freeze-drying (Agricultural Biolochemistry, 54, 1803–1810 (1990)). Furthermore, an acid-hydrolyzed peptide of lactoferrin can be obtained by adjusting lactoferrin dissolved in water to a concentration of 5% to pH 2 with concentrated hydrochloric acid and heating it at 120° C. for 15 minutes (Journal of Daily Science, 74, 3724–3730 (1991)).

Lactoferrin with an enhanced cell affinity can also be used. Such enhancement of cell affinity can be carried out by the chemical modification of the amino group in lactoferrin with amidination or guanidilation, or by the peptide bonding using a peptide containing basic amino acid such as arginine or lysine (Japanese Patent Laid-open (kokai) No. 207100/1990), or by introducing spermine or spermidine into the carboxyl group or the amino group (Japanese Patent Laid-Open (Kokai) No. 95100/1992).

The above-mentioned iron-binding proteins, chemically modified compounds, or partial hydrolysates can be used individually or together as a mixture as a composition for inhibiting HIV infection or suppressing HIV growth. Such a composition can be administered in various manners and can be formed into a variety of preparations, such as preparations for oral administration; injections; preparations for application to the skin, eye, ear, or nose; preparations for vagina washing or mouth washing; suppositories; and the like. It may be in the form of powder, tablet, solution, jelly, cream, or the like. It can be applied to a contraceptive device for preventing the HIV infection during sexual intercourse. For the prevention of HIV infection or HIV growth, the composition is normally administered at a dose of 1 mg to 1,000 mg, as lactoferrin, transferrin, or ovotransferrin, for adult 1 to 3 times a day. The dose, however, is reduced or increased depending on the expected effects and the symptoms.

Lactoferrin, transferrin, and ovotransferrin, which are iron-binding proteins used in the present invention, are contained in milk, egg white, and blood, respectively. They are all confirmed to be safe.

The composition for inhibiting the infection or suppressing the growth of HIV have the following effects.

(1) It can not only prevent the HIV infection, but also prevent the virus from growing in vivo and the infected cells from increasing.

(2) Since the effective components are compounds usually taken as foods by human, there are little risks of side effects due to administration of the composition.

(3) Since the raw materials are comparatively abundantly available, the production cost is significantly cheaper than that of conventional anti-HIV agents.

(4) The composition can be prepared by comparatively easier and in a larger amount than conventional anti-HIV agents. It can therefore prevent HIV infection and growth on a broad basis, without the application being limited only to specific patients.

Other features of the invention will become apparent in the following description of the exemplary embodiment which is given for illustration of the invention and is not intended to be limiting thereof.

EXAMPLE

Example 1

Preparation of Bovine Lactoferrin

Bovine lactoferrin was prepared from cow milk using the anti-bovine lactoferrin antibody affinity column disclosed in Journal of Daily Science, 20, 752–759 (1987). Skim milk was loaded onto an anti-bovine lactoferrin monoclonal antibody affinity column to adsorb the bovine lactoferrin. The column was thoroughly washed with a phosphate buffer saline (PBS, pH 7.3), then with PBS (pH 7.3) containing 0.5M sodium chloride. The lactoferrin adsorbed in the column was eluted with a 0.2M sodium acetate buffer solution (pH 3.7, containing 0.15M sodium chloride). After adjusting the pH to around neutral, the eluate was dialyzed against deionized water for 3 days, followed by lyophilization to obtain lactoferrin. The purity of the bovine lactoferrin thus obtained was confirmed by the electrophoresis.

Example 2

Preparation of Human Lactoferrin

Human lactoferrin was prepared from human milk using a heparin-sepharose CL6B column.

Skimmed human milk was loaded onto a heparin-Sepharose CL6B column to adsorb the human lactoferrin. The column was thoroughly washed with a 0.01M phosphate buffer solution (pH 7.3). The lactoferrin adsorbed in the column was eluted with a 0.01M phosphate buffer solution (pH 7.3) containing 1.0M sodium chloride. After adjusting the pH to approximately 7, the eluate was dialyzed against deionized water for 3 days, followed by lyophilization to obtain lactoferrin. The purity of the human lactoferrin thus obtained was confirmed by the electrophoresis.

Example 3

Preparation of Ovotransferrin

Ammonium sulfate was added to egg white to a concentration of 2.5M to precipitate proteins. The precipitate was collected by centrifuge, dissolved again in a 0.01M phosphate buffer (pH 6.0), and loaded onto a diethylaminoethyl cellulose column. The ovotransferrin in the egg white adsorbed in the column was washed with a 0.01M phosphate buffer (pH 6.0), eluted with a phosphate buffer (pH 6.0) containing 0.1M NaCl. After the elution, pH was adjusted close to neutral. The eluate was then dialyzed for 3 days against deionized water and freeze-dried to obtain ovotransferrin. The purity of the ovotransferrin thus obtained was confirmed by electrophoresis.

Example 4

Preparation of hydrolysates of iron-binding protein

Hydrolysis of lactoferrin was carried out by the trypsin treatment, the pepsin treatment, and the acid treatment.
(1) Trypsin treatment 100 mg of lactoferrin was dissolved in 10 ml of a 0.1M Tris-HCl buffer solution (pH 8.2) containing 25 mM calcium chloride. 2 mg of trypsin (a product of Sigma Co.) was added and the mixture was incubated at 37° C. for 4 hours. The trypsin was inactivated by 4 mg of soybean trypsin inhibitor and fractionated by the molecular sieving chromatography using Biogel P-30 (a product of Bio Lad Co.) which was equilibrated by 10% acetic acid.

The fractions were freeze-dried to obtain C-fragment with a molecular weight of 50,000 and N-fragment with a molecular weight of 30,000, each in an amount of about 3 mg.
(2) Pepsin treatment 100 mg of lactoferrin was dissolved in 10 ml of a 0.01M HCl solution and adjusted to pH 1.4. After the addition of 2 mg of pepsin (a product of Sigma Co.), the mixture was incubated at 37° C. for 6 hours. After the hydrolysis, the reaction was terminated by neutralizing the product to pH 7.0 with the addition of sodium hydroxide. 9 mg of highly hydrolyzed lactoferrin was obtained by this treatment. The content of the low molecular weight fraction (6% trichloro acetic acid soluble component) was 60%.
(3) Acid treatment 1 g of lactoferrin was dissolved in 20 ml of water and adjusted to pH 2.0 with concentrated hydrochloric acid (12N). The solution was sealed in a pressure-resistant glass container and heated at 120° C. for 15 minutes in an autoclave. After the heating, the steam was promptly discharged from the autoclave to cool the lactoferrin solution to room temperature. The insoluble components were removed by centrifuge at 10,000×G for 20 minutes. The supernatant was freeze-dried to obtain 0.6 g of an acid hydrolyzed peptide of lactoferrin.

Example 5

Preparation of chemically modified lactoferrin
(1) Preparation of tetrapeptide-introduced lactoferrin Human lactoferrin with an enhanced cell affinity was prepared by the introduction of tetrapeptide according to the method disclosed in Japanese Patent Laid-open (kokai) No. 207100/1990.

Peptides having the following sequence were used after activation of the carboxyl group in the C-terminal amino acid with N-hydroxysuccinimide and protection of the amino group in the N-terminal amino acid with methylsulfonyl-ethyl-oxycarbonyl.

Gly-Arg-Arg-Gly (SEQ ID NO. 1)
Gly-Arg-Arg-Arg-Arg-Gly (SEQ ID NO. 2)
Gly-Arg-Lys-Gly (SEQ ID NO. 3)
Gly-Lys-Lys-Gly (SEQ ID NO. 4)

The above peptides were added to human lactoferrin in an amount of 200 to 1,000 equivalent to 1 mol of the lactoferrin and the mixture was stirred overnight at 0°–10° C. to introduce the peptides. After completion of the reaction, pH was adjusted to 12 with 0.1N sodium hydroxide solution, then decreased to 5–6 with 0.1N hydrochloric acid to remove the protective group of the amino group. Furthermore, the mixture was dialyzed against PBS, pH 7.3, for 3 days to remove the free peptides.

As a result, a lactoferrin with an increased cell affinity, in which 10–15 mols of lactoferrin were introduced per 1 mol of a peptide, was prepared.
(2) Preparation of polyamine-introduced lactoferrin A human lactoferrin with an enhanced cell affinity was prepared by the introduction of polyamine according to a method disclosed in Japanese Patent Laid-open (kokai) No. 95100/1992.

348 mg of spermine tetrahydrochloride (1 mM) or spermidine trihydrochloride (1 mM) was dissolved into 3 ml of dimethylformamide, followed by the addition of 0.56 ml of triethylamine ($Et_3N$) under ice cooling. To the mixture was further added 266 mg of 2-(methylsulfonyl)-ethyl-N-succinimidyl carbonate in three portions at an interval of 30 minutes under ice cooling. After 6 hours, 115 mg of N-hydroxysuccinimide and 180 mg of 1-ethyl-3-(3-dimethylaminopropyl)carbodiimide hydrochloride were added, and the mixture was stirred at room temperature for 8 hours. The reaction mixture was concentrated under vacuum to obtain the target chemically modified reagent as a residue. The reagent was dissolved in 1 ml of deionized water for storing.

8 mg of human lactoferrin was dissolved into 1 ml of 0.1M phosphate buffer solution (pH 7.8). 200 µl of the above reagent was added to the solution under ice cooling, followed by stirring for 12 hours. After the reaction, the resultant reaction liquid was adjusted to pH 12 with 0.1N sodium hydroxide solution, then immediately to pH 5–7 with 0.1N hydrochloric acid to remove the protecting group, following which it was dialyzed against a phosphate buffer saline (PBS), pH 7.3, for 3 days to remove the free modification agent, thus obtaining a polyamine-introduced lactoferrin.

Example 6

Preparation of HIV infection-growth inhibitor

Injection preparations comprising the iron-binding proteins prepared in Examples 1–3 are presented in this example.

| (1) Bovine lactoferrin | 100 mg |
|---|---|
| Human serum albumin | 100 mg |

The above components were dissolved in PBS to make the total volume 20 ml, sterilized, charged into 2 ml vials, freeze-dried, and sealed.

| (2) Human lactoferrin | 100 mg |
|---|---|
| Tween 80 | 1 mg |
| Human serum albumin | 100 mg |

The above components were dissolved in physiological saline for injection use to make the total volume 20 ml, sterilized, charged into 2 ml vials, freeze-dried, and sealed.

| (3) Ovotransferrin | 100 mg |
|---|---|
| Tween 80 | 1 mg |
| Sorbitol | 4 mg |

The above components were dissolved in PBS to make the total volume 20 ml, sterilized, charged into 2 ml vials, freeze-dried, and sealed.

| (4) Bovine lactoferrin | 4 g |
|---|---|
| Tween 80 | 2 mg |
| Glycine | 2 g |

The above components were dissolved in physiological saline for injection use to make the total volume 20 ml, sterilized, charged into 2 ml vials, freeze-dried, and sealed.

| (5) Human lactoferrin | 4 g |
|---|---|
| Tween 80 | 1 mg |
| Sorbitol | 2 g |
| Glycine | 1 g |

The above components were dissolved in physiological saline for injection use to make the total volume 20 ml, sterilized, charged into 2 ml vials, freeze-dried, and sealed.

| (6) Ovotransferrin | 4 g |
|---|---|
| Sorbitol | 4 g |
| Human serum albumin | 50 mg |

The above components were dissolved in PBS to make the total volume 20 ml, sterilized, charged into 2 ml vials, freeze-dried, and sealed.

Experimental Example 1

Assay for anti-HIV activity of lactoferrin and transferrin
(Method)

The culture liquid supernatant of MOLT-4/HTLV-III$_B$, which is a TLV-III$_B$ persisting infectious cell, belonging to the HIV cell line (Ikuta et al. Medical Topics, 4, 41 (1988)), was used as the virus liquid. The supernatant was stored at −80° C. MT-4 cell of human T-cell line was used as a cell for the assay. MT-4 was subcultured in RPMI1640 medium containing 10% fetal calf serum (FCS). The samples (human lactoferrin and bovine transferrin) were dissolved into the medium (RPMI1640), sterilized by filter, and added to the cell.

1 ml of the sample, diluted to different concentrations, was added to a 24-well microculture plate. MT-4 cells were infected with HIV at a moi (multiplicity of infection; the ratio of cells/infection virus) of 0.01. 1 ml of the cell suspension with a concentration of $3 \times 10^5$ cells/ml was added and the cells were cultured for 3 days, following which the HIV-infected cells were measured by the indirect fluorescent antibody method.

The measurement of the HIV-infected cells was carried out by the indirect fluorescent antibody method using serum of an HIV-infected patient as a primary antibody. More than 500 cells were observed under a fluorescent microscope to calculate the proportion of cells stained with fluorescent.

HIV-infected MT-4 cells cultured without the addition of the sample and cells cultured without the addition of virus were used respectively as a positive control and a negative control.

(Results)

The results of the experiment are shown in Table 1, in which the results are indicated by the proportion of the stained cells. The stained ratio of the HIV-infected MT-4 cells of the positive control was 26.0%, whereas stained ratio of the MT-4 cells, to which no HIV was added, was 0%.

The human lactoferrin decreased the infection ratio to ⅓ at a concentration of 125 µg/ml, while the bovine transferrin was confirmed to decrease the infection ratio to some degree.

TABLE 1

| Sample | Concentration | | | | |
|---|---|---|---|---|---|
|  | 1000 | 500 | 250 | 125 | 63 |
| Human lactoferrin | 3.1 | 5.8 | 7.3 | 8.6 | 17 |
| Bovine transferrin | 20 | 20 | 18 | 19 | 23 |

Experimental Example 2

Differences in the anti-HIV activity depending on the time of sample administration
(Method)

The following experiments were performed using the same virus and cell as in Experimental Example 1.

Experiment 1

MT-4 cells were incubated together with the sample (1 mg/ml) for 60 minutes in advance. The cells were contacted with HIV at moi=1 for 1 hour in the presence of the sample, and then cells were washed to remove the sample and virus, followed by cultivation for 3 days.

Experiment 2

The same procedure as above was followed, except that the sample was added only when virus was contacted.

Experiment 3

The same procedure as Experiment 1 was followed, except that the sample was added when cultured after the contact with virus.

The proportion of stained cells in each experiment was measured by the fluorescent antibody method. The ratio of HIV-infected cells was determined in the same manner as in Experimental Example 1.
(Results)

The results are shown in Table 2, wherein "+" indicates the cases where the sample was added and "−" indicates the cases where no sample was added. Since HIV with moi=1 was used in this experiment, the staining ratio of the positive control was 100%. The staining ratio of the negative control was 0%.

The anti-HIV effect was higher when the sample was added to the MT-4 cells in advance. The bovine lactoferrin had a particularly strong HIV activity and, if acted before the infection, could completely suppressed the infection by the high titer HIV of moi=1. Human lactoferrin also exhibited a strong anti-HIV effect.

TABLE 2

| | Timing of the sample addition | | | |
|---|---|---|---|---|
| | (Experiment 1) Before infection | (Experiment 2) During infection | (Experiment 3) After infection | HIV infection ratio (%) |
| Human lactoferrin | + | + | − | 9.9 |
| | − | + | − | 4.9 |
| | − | − | + | 52 |
| Bovine lactoferrin | + | + | − | 0 |
| | − | + | − | 3.4 |
| | − | − | + | 17 |
| Human transferrin | + | + | − | 22 |
| | − | + | − | 86 |
| | − | − | + | 52 |

Experimental Example 3

Anti-HIV activity of ovotransferrin (Method)

The anti-HIV activity of ovotransferrin obtained by the method of Example 3 was measured by the method of Experimental Example 2 (Experiment 1). Ovotransferrin was added to the concentration of 1 mg/ml. HIV was added at moi=1.

(Results)

The result is shown in Table 3, which indicates that ovotransferrin possessed an anti-HIV activity, although the activity slightly lower than that of lactoferrin.

TABLE 3

| Sample | HIV-infection ratio (%) |
|---|---|
| Ovotransferrin | 18 |

Experimental Example 4

Anti-HIV activity of lactoferrin hydrolysates (Method)

The anti-HIV activities of limited trypsin hydrolyzed compound, the pepsin hydrolyzed compound, and the acid hydrolysate, of human lactoferrin obtained in Example 4 were measured according to the method of Experimental Example 2 (Experiment 1). Each hydrolysate was added to the concentration of 1 mg/ml. HIV was added at moi=1.

(Results)

The results are shown in Table 4, which shows that all hydrolysates possessed an anti-HIV activity, indicating their possession of a fragment exhibiting anti-HIV activity.

TABLE 4

| Sample Lactoferrin | HIV-infection ratio (%) |
|---|---|
| Trypsin hydrolysate | 14 |
| Pepsin hydrolysate | 26 |
| Acid hydrolysate | 33 |

Obviously, numerous modifications and variations of the present invention are possible in light of the above teachings. It is therefore to be understood that within the scope of the appended claims, the invention may be practiced other than as specifically described herein.

What is claimed is:

1. A method for inhibiting and suppressing growth of human immunodeficiency virus in lymphoid cells comprising the steps of:
(a) providing at least one iron-binding protein selected from the group consisting of:
(1) lactoferrin, ovotransferrin and
(2) derivatives of lactoferrin and ovotransferrin, wherein said derivatives are selected from the group consisting of:
(i) lactoferrin and ovotransferrin peptide conjugates wherein said lactoferrin or said ovotransferrin is conjugated with a peptide consisting essentially of basic amino acids, and
(ii) lactoferrin and ovotransferrin polyamine conjugates wherein said lactoferrin or said ovotransferrin is conjugated with a polyamine; and,
(b) contacting lymphoid cells susceptible to infection by human immunodeficiency virus, with an effective anti-viral amount of said iron-binding protein, said protein being competent to inhibit infection by or suppress growth of human immunodeficiency virus in said cells.

2. The method of claim 1 wherein said peptide is selected from the group consisting of: Gly-Arg-Arg-Gly (Seq. ID No. 1), Gly-Arg-Arg-Arg-Arg-Gly (Seq. ID No.: 2), Gly-Arg-Lys-Gly (Seq. ID No.: 3) and Gly-Lys-Lys-Gly (Seq. ID No.: 4).

3. The method of claim 1 wherein said basic amino acids are selected from the group consisting of: glycine, arginine and lysine.

4. The method of claim 1 wherein said polyamine is selected from spermine and spermidine.

5. A method for inhibiting and suppressing growth of human immunodeficiency virus in lymphoid cells comprising the steps of:
(a) providing at least one iron-binding protein comprising hydrolyzed derivatives of lactoferrin, wherein said derivatives are selected from the group consisting of:
(i) trypsin hydrolysates of lactoferrin, said hydrolysates containing carboxy terminal fragments with a molecular weight of about 50 kD as determined by gel filtration and amino terminal fragments with a molecular weight of about 30 kD as determined by gel filtration,
(ii) pepsin hydrolysates of lactoferrin, said hydrolysates containing 60% of a 6% trichloroacetic acid soluble component and
(iii) acid hydrolysates of lactoferrin, said hydrolysates consisting essentially of soluble components; and,
(b) contacting lymphoid cells susceptible to infection by human immunodeficiency virus, with an effective anti-viral amount of said iron-binding protein, said protein being competent to inhibit infection by or suppress growth of human immunodeficiency virus in said cells.

6. A composition comprising:
an effective anti-viral amount of at least one iron-binding protein comprising derivatives of lactoferrin and ovotransferrin, wherein said derivatives are selected from the group consisting of:
(i) lactoferrin and ovotransferrin peptide conjugates wherein said lactoferrin or said ovotransferrin is conjugated with a peptide consisting essentially of basic amino acids and (ii) lactoferrin and ovotransferrin polyamine conjugates wherein said lactoferrin or said ovotransferrin is conjugated with a polyamine, said composition being competent to inhibit infection by or suppress growth of human immunodeficiency virus.

7. The composition of claim 6 wherein said peptide is selected from the group consisting of: Gly-Arg-Arg-Gly (Seq. ID No. 1), Gly-Arg-Arg-Arg-Arg-Gly (Seq. ID No.: 2), Gly-Arg-Lys-Gly (Seq. ID No.: 3) and Gly-Lys-Lys-Gly (Seq. ID No.: 4).

8. The composition of claim 6 wherein said basic amino acids are selected from the group consisting of: glycine, arginine and lysine.

9. The composition of claim 6 wherein said polyamine is selected from spermine and spermidine.

10. The composition of claim 6 wherein said lactoferrin is obtained from milk of mammals or fluids secreted by mammals.

11. The composition of claim 6 wherein said ovotransferrin is obtained from egg white.

12. A method of suppressing infection by human immunodeficiency virus comprising the step of:

contacting a lymphoid cell susceptible to infection by, but not yet infected with said virus, with an effective anti-viral amount of an iron-binding protein, said iron-binding protein selected from the group consisting of: bovine lactoferrin, bovine lactoferrin conjugated with the peptide Gly-Arg-Arg-Gly (Seq. ID No. 1) and a pepsin hydrolysate of bovine lactoferrin, said hydrolysate containing at least 60% of a 6% trichloroacetic acid soluble component.

13. A composition for suppressing infection by human immunodeficiency virus comprising:

an effective anti-viral amount of an iron-binding protein, said iron-binding protein selected from the group consisting of: bovine lactoferrin conjugated with the peptide Gly-Arg-Arg-Gly (Seq. ID No. 1) and a pepsin hydrolysate of bovine lactoferrin, said hydrolysate containing at least 60% of a 6% trichloroacetic acid soluble component of low molecular weight.

* * * * *

UNITED STATES PATENT AND TRADEMARK OFFICE
CERTIFICATE OF CORRECTION

PATENT NO. : 5,725,864
DATED : March 10, 1998
INVENTOR(S) : Yamamoto et al.

It is certified that error appears in the above-identified patent and that said Letters Patent is hereby corrected as shown below:

On the title page in item [57] ABSTRACT, lines 7 to 9, the sentence reading "The effective components are safe and can be easily prepared from inexpensive raw materials." should be deleted.
In Claim 13 the last four words reading "of low molecular weight" should be deleted.

Signed and Sealed this

Eighth Day of December, 1998

*Attest:*

BRUCE LEHMAN

*Attesting Officer*  *Commissioner of Patents and Trademarks*